US012773218B2

(12) United States Patent
Huang et al.

(10) Patent No.: US 12,773,218 B2
(45) Date of Patent: Oct. 27, 2026

(54) TOURNIQUET WITH MULTI-ANGLE TIGHTENING DEVICE

(71) Applicant: Chu-hsiung Huang, Taichung City (TW)

(72) Inventors: Chu-hsiung Huang, Taichung City (TW); Hao-cheng Fan, Taichung City (TW)

( * ) Notice: Subject to any disclaimer, the term of this patent is extended or adjusted under 35 U.S.C. 154(b) by 362 days.

(21) Appl. No.: 18/482,160

(22) Filed: Oct. 6, 2023

(65) Prior Publication Data

US 2024/0148391 A1 May 9, 2024

(30) Foreign Application Priority Data

Nov. 7, 2022 (TW) .................................. 111142474

(51) Int. Cl.
*A61B 17/132* (2006.01)

(52) U.S. Cl.
CPC ................................ *A61B 17/1325* (2013.01)

(58) Field of Classification Search
CPC .............. A61B 17/132; A61B 17/1322; A61B 17/1325; A61B 17/1327
See application file for complete search history.

(56) References Cited

U.S. PATENT DOCUMENTS

| | | | | |
|---|---|---|---|---|
| 3,050,064 | A * | 8/1962 | Moore | A61B 17/1325 606/203 |
| 2012/0150215 | A1* | 6/2012 | Donald | A61B 17/1325 606/203 |
| 2015/0216536 | A1 | 8/2015 | Hopman et al. | |
| 2016/0375969 | A1 | 12/2016 | Henderson et al. | |
| 2018/0193033 | A1 | 7/2018 | Kosiorek et al. | |
| 2021/0153873 | A1 | 5/2021 | Peterson et al. | |
| 2022/0039805 | A1* | 2/2022 | Hsiao | A61B 17/1327 |
| 2022/0047273 | A1 | 2/2022 | Parsons et al. | |

* cited by examiner

*Primary Examiner* — Diane D Yabut

(57) ABSTRACT

A tourniquet with multi-angle tightening devices includes a tourniquet main body, a first tightening device, and a fixing element. The first tightening device is rotatably disposed on the tourniquet main body and includes at least three pillar-shaped structures. The at least three pillar-shaped structures respectively extends outward from a rotation center of the first tightening device. There is a first width between the at least three pillar-shaped structures. The fixing element is disposed adjacent to the first tightening device and is disposed on the tourniquet main body. The first width is wider than the second width of the fixing element. A distance from the rotation center of the first tightening device to the fixing element is less than an extension length of any one of the at least three pillar-shaped structures from the rotation center.

13 Claims, 22 Drawing Sheets

TOURNIQUET WITH MULTI-ANGLE TIGHTENING DEVICE

CROSS REFERENCE TO RELATED APPLICATIONS

This application is claims priority to Taiwanese Patent Application No. 111142474 filed Nov. 7, 2022, the contents of each application are hereby incorporated by reference in their entirety.

BACKGROUND OF INVENTION

Field of Invention

The present application relates to a tourniquet, and particular to a tourniquet with a multi-angle tightening device.

Description of Prior Art

Since ancient times, humans have found that using belts to tighten severed limbs, then coupled with sticks to tighten and pressurize, can effectively reduce blood loss.

However, most tourniquets in the prior art only have a single tightening device, for example, only one rod member, one ratchet, or one buckle, etc. Therefore, due to size difference between to-be-compressed limbs, when using the tightening device, it is difficult to ensure reliable compression, which is prone to cause insufficient pressure force.

In addition, in requirements of modern combat first aid, when personally operating a tourniquet, a person is required to complete all steps of pressurizing a limb within 15 seconds to prevent excessive blood loss. However, as mentioned above, because the tourniquets in the prior art have the aforesaid problems, when operated the tourniquet by one person, it is more difficult to complete the hemostasis steps within the time limit, causing many difficulties.

SUMMARY OF INVENTION

In the tourniquet with multi-angle tightening device of the present application, as the tightening device that can pressurize at multiple angles is used, the pressure force to a limb is sufficient, and efficiency of tourniquet usage is increased, so using the tourniquet is more convenient. Furthermore, in some embodiments of the present application, more than one tightening device is provided, which not only can achieve the aforesaid effects, but also has better reliability.

On the basis of the aforesaid purpose, the present application provides a tourniquet with a multi-angle tightening device, including a tourniquet main body, a first tightening device, and a fixing element. The first tightening device is rotatably disposed on the tourniquet main body and includes at least three pillar-shaped structures. The at least three pillar-shaped structures respectively extends outward from a rotation center of the first tightening device. There is a first width between the at least three pillar-shaped structures. The fixing element is disposed adjacent to the first tightening device and is disposed on the tourniquet main body. The first width is wider than the second width of the fixing element. A distance from the rotation center of the first tightening device to the fixing element is less than an extension length of any one of the at least three pillar-shaped structures from the rotation center.

Preferably, the tourniquet main body includes a first tightening strip, a second tightening strip, and a cover layer. A first portion and a second portion of the second tightening strip are connected to the first tightening strip, a third portion of the second tightening strip is movably disposed on the first tightening strip, and the cover layer covers the first tightening strip and the second tightening strip.

Preferably, the first tightening device is connected to the third portion of the second tightening strip through an opening of the cover layer.

Preferably, the fixing element includes at least one limit unit, a first curved portion, and a second curved portion. The at least one limit unit is disposed between the first curved portion and the second curved portion. The first curved portion forms a first groove. The second curved portion forms a second groove. Concave directions of the first groove and the second groove are opposite.

Preferably, the first tightening device is positioned against one of the first curved portion or the second curved portion.

Preferably, a first interval between the at least one limit unit and a top of a lateral wall of the first curved portion and a second interval between the at least one limit unit and a top of a lateral wall of the second curved portion are less than a thickness of the first tightening device.

Preferably, the multi-angle tightening device further includes a second tightening device. The second tightening device corresponds to the first tightening device and is disposed on the tourniquet main body, and the fixing element is disposed between the first tightening device and the second tightening device.

Preferably, the tourniquet main body includes a first tightening strip, a second tightening strip, and a cover layer. A first portion and a second portion of the second tightening strip are connected to the first tightening strip. A third portion of the second tightening strip is movably disposed on the first tightening strip. The cover layer covers the first tightening strip and the second tightening strip, and the first tightening device is connected to the third portion of the second tightening strip through an opening of the cover layer.

Preferably, a first attachment structure and a second attachment structure are respectively disposed on a bottom surface and a top surface of the tourniquet main body. After the tourniquet main body is wound around, the first attachment structure and the second attachment structure are attached to each other.

DETAILED DESCRIPTION OF EMBODIMENTS

In order to understand the technical features, content and advantages of the present application, and the effects which can achieve, the present application is hereby accompanied with the drawings and described in detail in the form of embodiments as follows. The drawings which are only for purpose of illustration and auxiliary explanation, and may not be the true proportion and precise configuration after the implementation of the present application. Therefore, it should not be interpreted based on the proportion and configuration relationship of the accompanied drawings, and limit the scope of rights of the present application in actual implementation.

The embodiments of the present application will be described below with reference to the relevant drawings. For ease of understanding, the same components in the following embodiments are described with the same symbols.

Please refer to FIG. 1 to FIG. 8, which are a first top view, first to second sectional views, first to fourth implementation schematic diagrams, a schematic diagram of a first tightening device, and a schematic diagram of a fixing element according to a tourniquet with a multi-angle tightening device of the present application.

The present application provides a tourniquet with a multi-angle tightening device, including a tourniquet main body 11, a first tightening device 12, and a fixing element 14. The first tightening device 12 is rotatably disposed on the tourniquet main body 11 and includes at least three pillar-shaped structures. The at least three pillar-shaped structures respectively extends outward from a rotation center of the first tightening device 12. There is a first width W1 between the pillar-shaped structures. The fixing element 14 is disposed adjacent to the first tightening device 12 and is disposed on the tourniquet main body 11.

Figure 1:
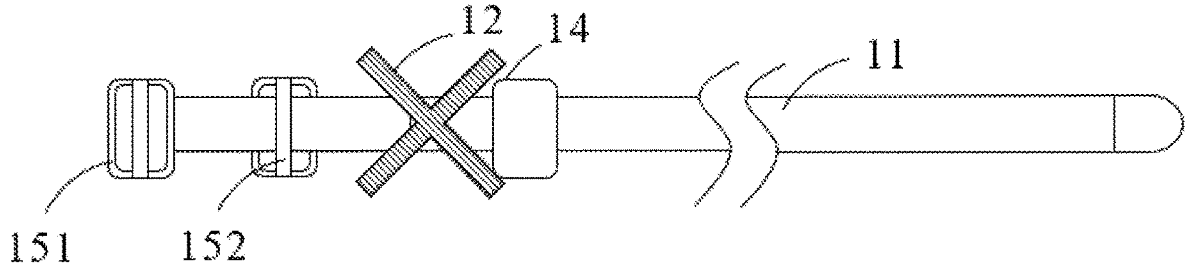
FIG. 1 is a first top view of a tourniquet with a multi-angle tightening device according to one embodiment of the present application.
Figure 2:
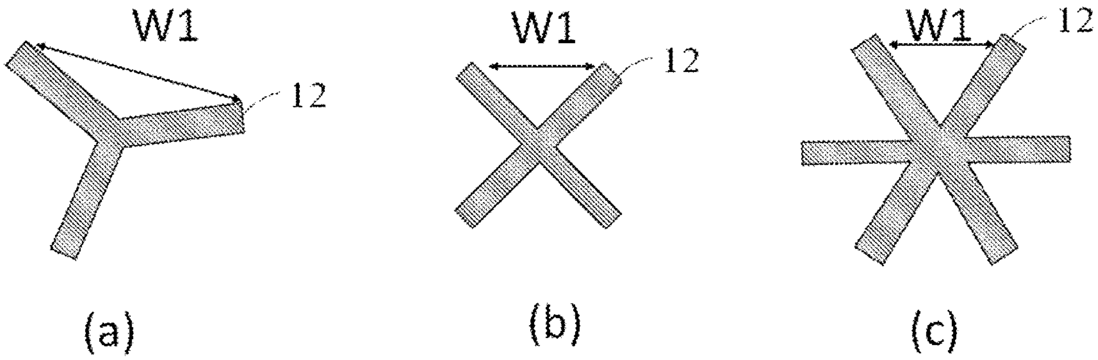
FIG. 2 is a schematic diagram of a first tightening device of the tourniquet with the multi-angle tightening device according to one embodiment of the present application.
Figure 3:
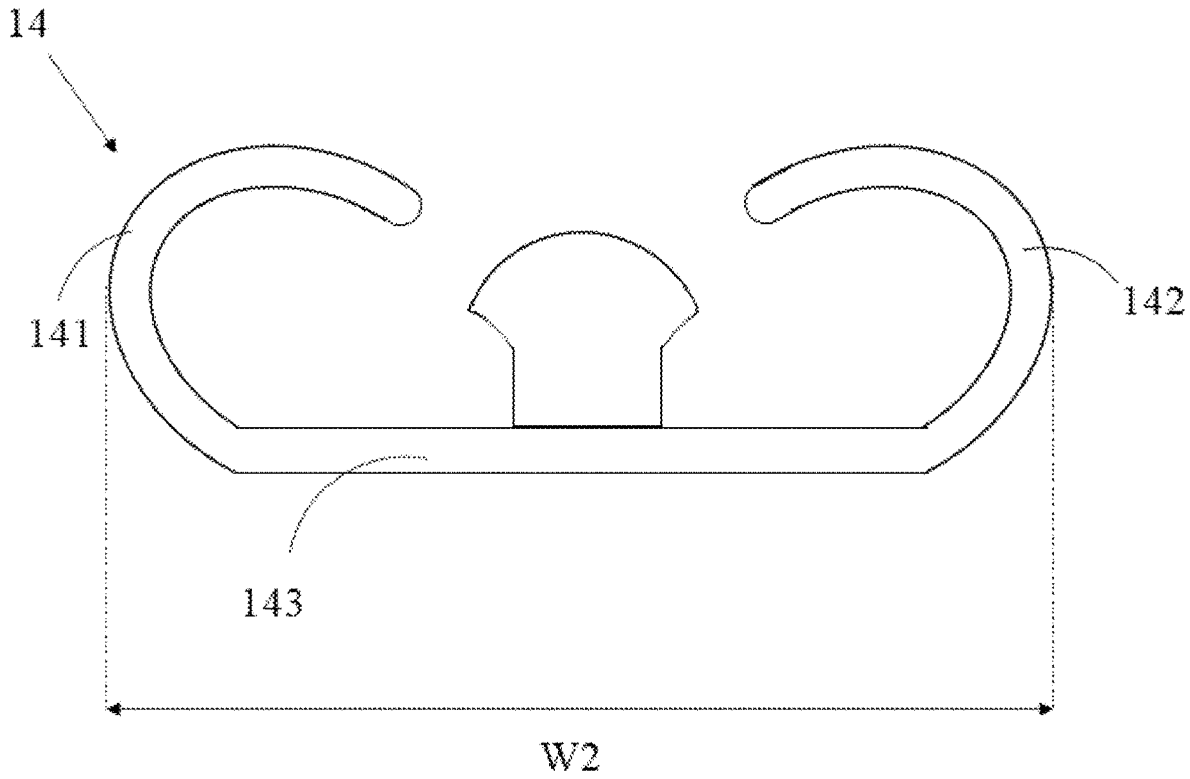
FIG. 3 is a schematic diagram of a fixing element of the tourniquet with the multi-angle tightening device according to one embodiment of the present application.

As illustrated in part (a) to part (c) of FIG. 2, a number of the pillar-shaped structures can be three, four, six, etc. In detail, the number of pillar-shaped structures can also be any number such as five or more than six. Furthermore, as illustrated in FIG. 2 and FIG. 3, the first width W1 is wider than the second width W2 of the fixing element 14 to avoid interference between the first tightening device 12 and the fixing element 14. In addition, a position defined by the first width W1 depends on the length of the pillar-shaped structure and a position of the fixing element 14.

A distance from the rotation center of the first tightening device 12 to the fixing element 14 is less than an extension length of any one of the pillar-shaped structures from the rotation center. In other words, the length of the pillar-shaped structures must be ensured to be sufficiently extended to the fixing element 14 so that the fixing element 14 can fix the position of the first tightening device 12.

In one embodiment, the tourniquet main body 11 can penetrate a first buckle 151 and a second buckle 152. Therefore, the length of the tourniquet main body 11 can be adjusted, and the position of the tourniquet main body 11 can be restricted. When hemostasis is required, the tourniquet main body 11 can be wound around the limb that needs hemostasis, and then the first tightening device 12 can be used to tighten the tourniquet main body 11, so that the tourniquet main body 11 can further pressurize the limb.

More detailly, taking the first tightening device 12 including three pillar-shaped structures as an example, when rotating the first tightening device 12, at most rotating for every 120 degrees, the position of the first tightening device 12 can be fixed by the fixing element 14.

Similarly, if the first tightening device 12 includes four pillar-shaped structures, when rotating the first tightening device 12, at most rotating for every 90 degrees, the position of the first tightening device 12 can be fixed by the fixing element 14.

Similarly, if the first tightening device 12 includes six pillar-shaped structures, when rotating the first tightening device 12, at most rotating for every 60 degrees, the position of the first tightening device 12 can be fixed by the fixing element 14. Therefore, the present invention is suitable to users of various body types.

Furthermore, the fixing element 14 includes at least one limit unit 143, a first curved portion 141, and a second curved portion 142. The at least one limit unit 143 can be disposed between the first curved portion 141 and the second curved portion 142. The first curved portion 141 forms a first groove. The second curved portion 142 forms a second groove. Concave directions of the first groove and the second groove are opposite.

Therefore, if the first tightening device 12 is rotated, the second tightening strip 112 will move toward a top surface of the cover layer 114, causing the tourniquet main body 11 to be tightened and to pressurize a limb. Furthermore, in one embodiment, in order to make the first tightening device 12 be not easily damaged, the first tightening device 12 can include aluminum alloy.

Figure 5:
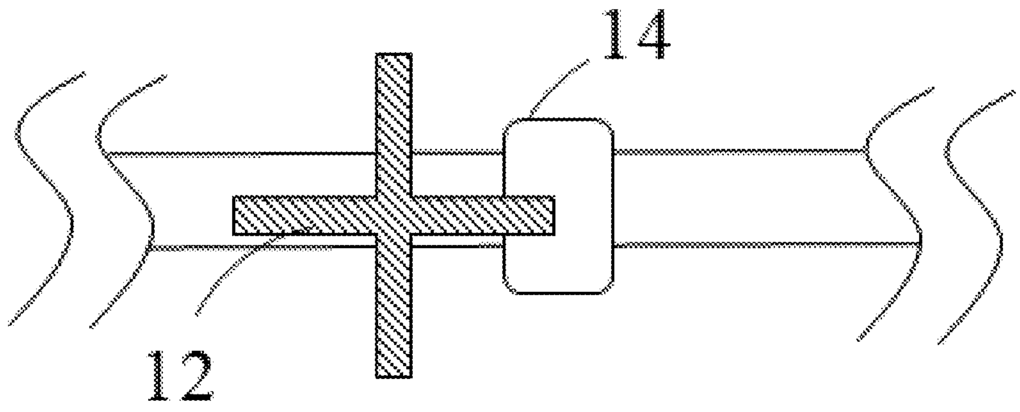
FIG. 5 is a first implementation schematic diagram of the tourniquet with the multi-angle tightening device according to one embodiment of the present application.
Figure 6:
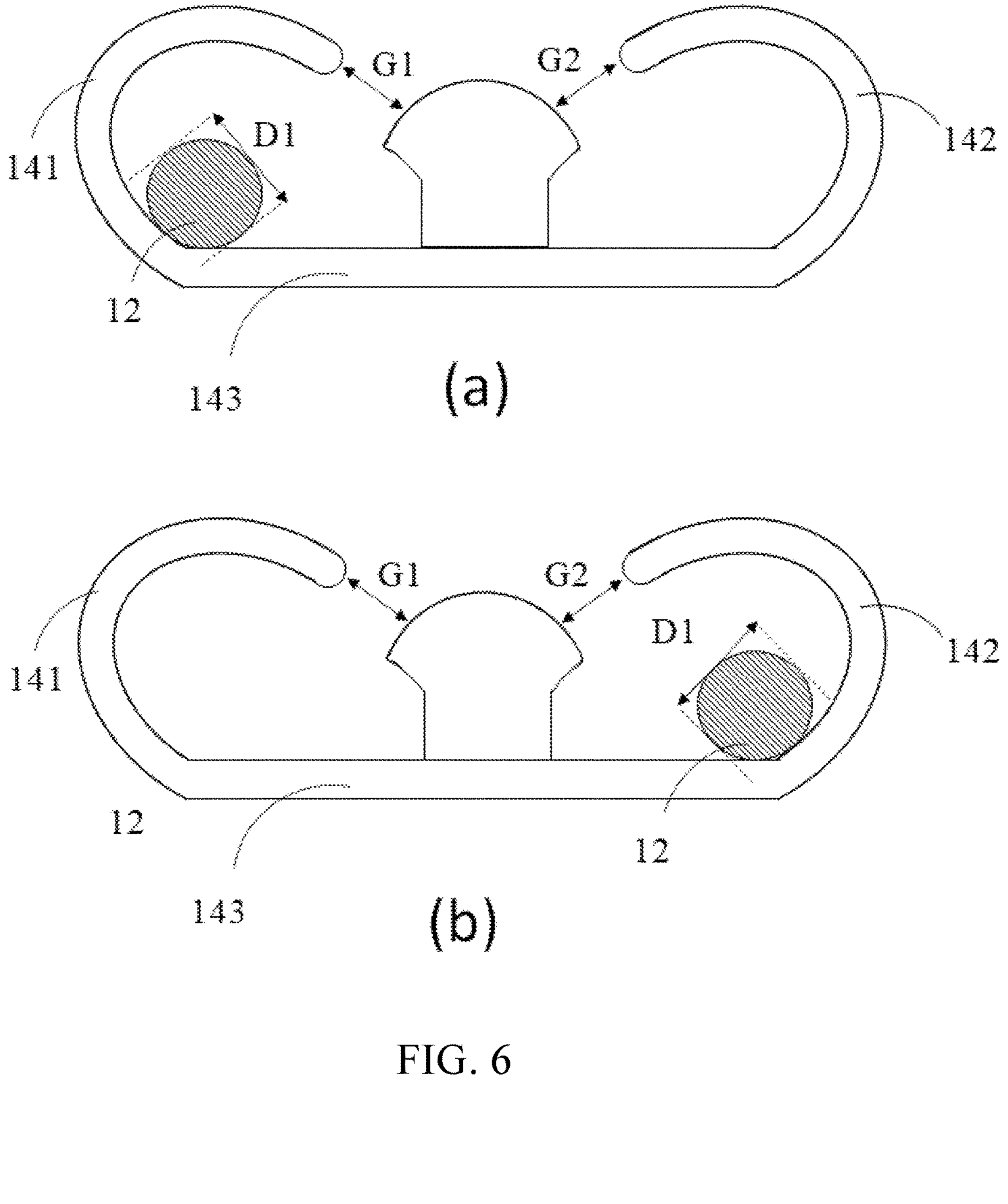
FIG. 6 is a second implementation schematic diagram of the tourniquet with the multi-angle tightening device according to one embodiment of the present application.
Figure 7:
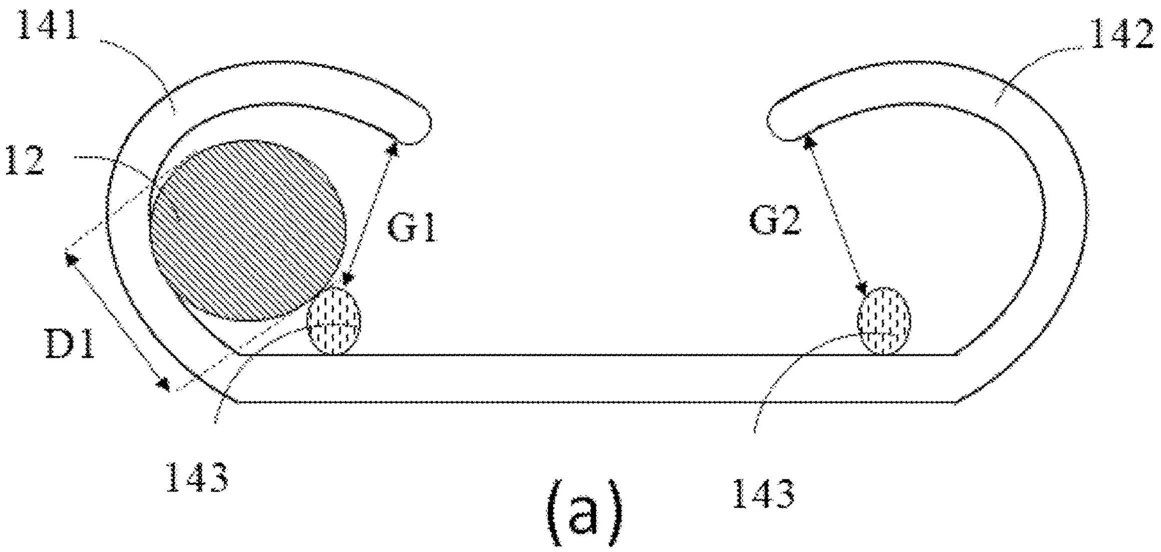
FIG. 7 is a third implementation schematic diagram of the tourniquet with the multi-angle tightening device according to one embodiment of the present application.
Figure 7:
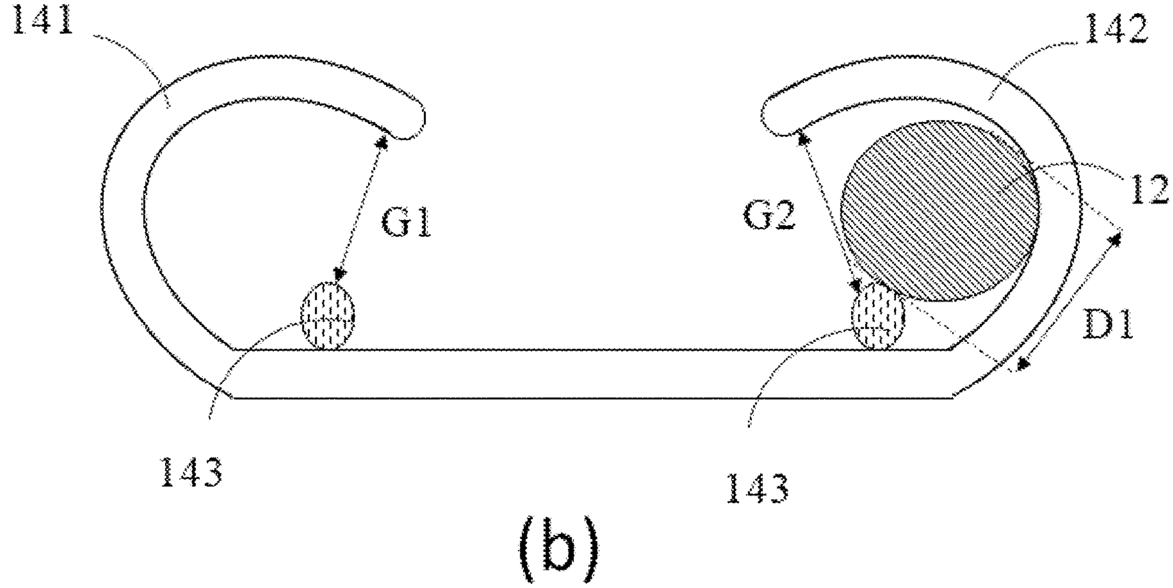

As illustrated in FIG. 5 to FIG. 7, in order to fix the first tightening device 12 and the second tightening device 13, the first tightening device 12 can be positioned against one of the first curved portion 141 or the second curved portion 142.

As illustrated in FIG. 6, in one embodiment, the limit unit 143 of the present application can be disposed between the first curved portion 141 and the second curved portion 142. For example, the limit unit 143 can be disposed at the center of the fixing element 14. The limiting unit 143 can be made of elastic material, such as polypropylene (Polypropylene, PP). A first interval G1 between the limit unit 143 and the top of the lateral wall of the first curved portion 141, and a second interval G2 between the limit unit 143 and the top of the lateral wall of the second curved portion 142 are less than a thickness D1 of the first tightening device 12 and the second tightening device 13.

Therefore, after the first tightening device 12 passes through the first curved portion 141 or the second curved portion 142, and the limit unit 143; the first tightening device 12 is restricted in the first curved portion 141 or the second curved portion 142.

Furthermore, a top of the limit unit 143 can be a three-dimensional structure with a smooth curved surface such as a hemisphere, an ellipsoid, etc., and the tops of the lateral walls of the first curved portion 141 and the second curved portion 142 can be rounded or chamfered to facilitate the first tightening device 12 and the second tightening device 13 to slide through.

As illustrated in FIG. 7, in another embodiment, the limit unit 143 of the present application can also be disposed at another position. For example, two limit units 14 can be respectively disposed at the top of the lateral walls of the first curved portion 141 and the second curved portion 142 adjacent to the fixing element 14. The limiting units 143 can also be made of elastic material, such as polypropylene (Polypropylene, PP). The first interval G1 between the limit unit 143 and the top of the lateral wall of the first curved portion 141, and the second interval G2 between the limit unit 143 and the top of the lateral wall of the second curved portion 142 are less than the thickness D1 of the first tightening device 12 and the second tightening device 13.

Figure 8:
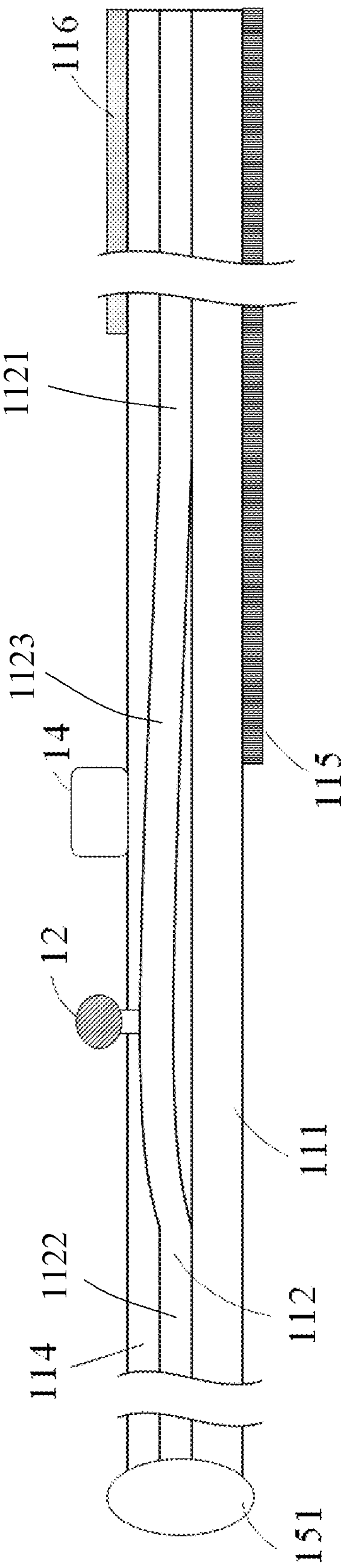
FIG. 8 is a second sectional view of the tourniquet with the multi-angle tightening device according to one embodiment of the present application.

In one embodiment, as illustrated in FIG. 8, the tourniquet main body 11 includes a first tightening strip 111, a second tightening strip 112, and a cover layer 114. As illustrated in FIG. 8, a first portion 1121 and a second portion 1122 of the second tightening strip 112 are connected to the first tightening strip 111, and a third portion 1123 of the second tightening strip 112 is movably disposed on the first tightening strip 111. The cover layer 114 can cover the first tightening strip 111 and the second tightening strip 112. The first tightening device 12 is connected to the third portion 1123 of the second tightening strip 112 through an opening of the cover layer 114.

In detail, the first portion 1121 and the second portion 1122 of the second tightening strip 112 can be respectively located at two ends of the first tightening strip 111. The first portion 1121 of the second tightening strip 112 can be sewed together with the first tightening strip 111, and the second portion 1122 of the second tightening strip 112 and one end of the first tightening strip 111 can be connected to the first buckle 151.

Furthermore, in this embodiment, the first interval G1 between the limit unit 143 and the top of the lateral wall of the first curved portion 141, and the second interval G2 between the limit unit 143 and the top of the lateral wall of the second curved portion 142 are less than the thickness D1 of the first tightening device 12. Therefore, similar to the embodiment in which the limit unit 143 is disposed at the center of the fixing element 14, the first tightening device 12 can be restricted in the first curved portion 141 and the second curved portion 142.

Similarly, in this embodiment, the top of the limit unit 143 can also be a three-dimensional structure with a smooth curved surface such as a hemisphere, an ellipsoid, etc., and the tops of the lateral walls of the first curved portion 141 and the second curved portion 142 can be rounded or chamfered to facilitate the first tightening device 12 and the second tightening device 13 to slide through.

Figure 4:
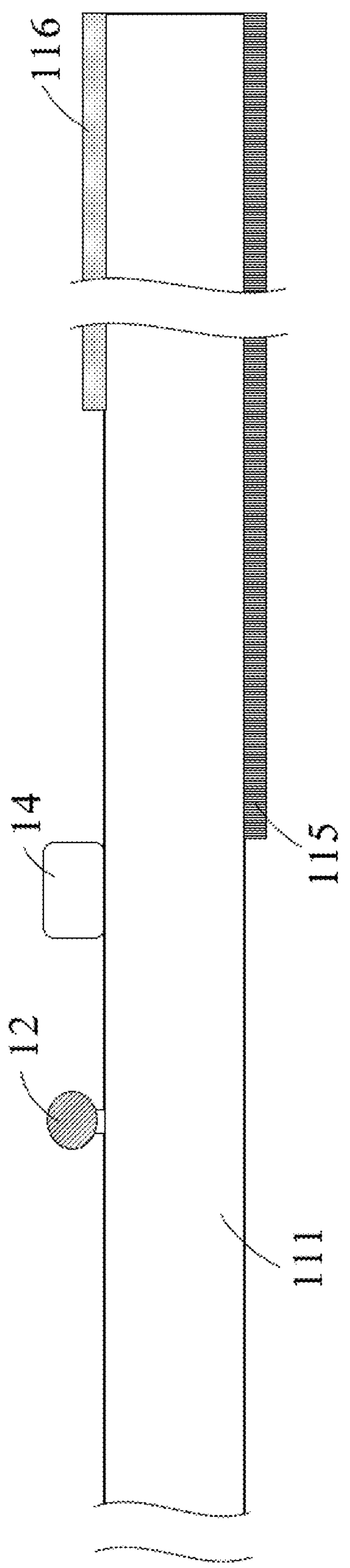
FIG. 4 is a first sectional view of the tourniquet with the multi-angle tightening device according to one embodiment of the present application.

In addition to the aforesaid embodiment including the second tightening strip 112, the present application can also have other implementation forms. As illustrated in FIG. 4, the second tightening strip 112 and the third tightening strip 113 can also need not to be provided in the tourniquet with the multi-angle tightening device of the present application. In detail, the first tightening device 12 can be directly disposed on the first tightening strip 111. As illustrated in FIG. 4, when the first tightening device 12 includes pillar-shaped structures, the fixing element 14 needs to be provided. When the first tightening device 12 is a ratchet or other tightening device that can fix its own position, the fixing element 14 can be omitted.

In addition to the aforesaid embodiments, as illustrated in FIG. 9 to FIG. 16, in order to realize the multi-angle tightening function, the tourniquet with the multi-angle tightening device of the present invention can further include a second tightening device 13. The second tightening device 13 can correspond to the first tightening device 12 and is disposed on the tourniquet main body 11. The fixing element 14 is disposed between the first tightening device 12 and the second tightening device 13.

Figure 9:
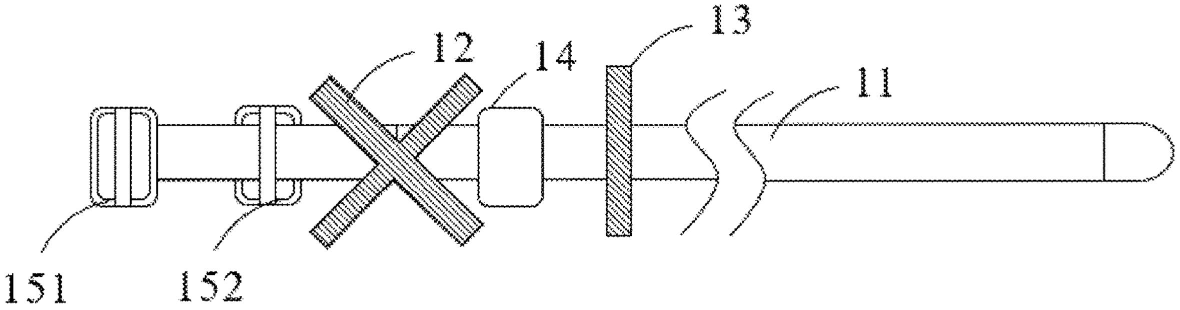
FIG. 9 is a second top view of the tourniquet with the multi-angle tightening device according to one embodiment of the present application.
Figure 10:
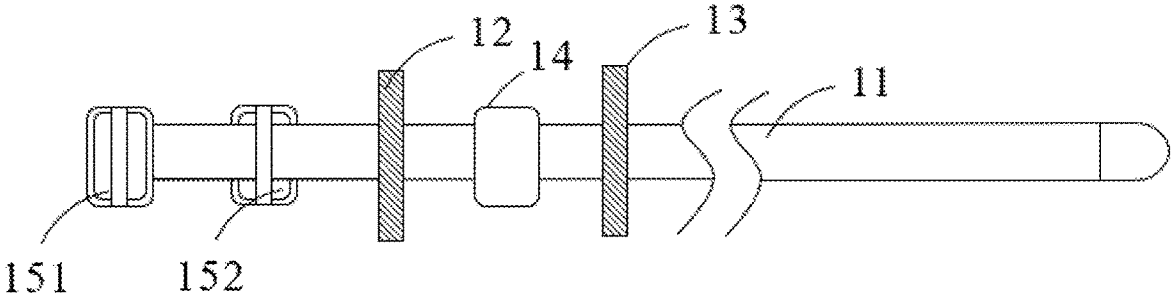
FIG. 10 is a third top view of the tourniquet with the multi-angle tightening device according to one embodiment of the present application.

In one embodiment, as illustrated in FIG. 9 to FIG. 10, as there is the second tightening device 13, the first tightening device 12 can include at least two pillar-shaped structures, which form a rod member, and the second tightening device 13 can also be a rod member.

In one embodiment, the tourniquet main body 11 can be wound around the limb which needs hemostasis, and then the tourniquet main body 11 can be tightened by the first tightening device 12, so that the tourniquet main body 11 can further pressurize the limb. After that, the first tightening device 12 is fixed in position by the fixing element 14. Besides, due to differences in the limb sizes among individuals, when the first tightening device 12 is fixed by the fixing element 14, the pressure force to the limbs may not be enough. At this time, the second tightening device 13 can be used to make the tourniquet main body 11 to be further tightened, thereby making the tourniquet main body 11 can further pressurize the limb, thus achieving the effect of multi-angle tightening.

In this embodiment, as the first tightening device 12 can also include at least three pillar-shaped structures (for example, the first tightening device 12 in FIG. 9 includes four pillar-shaped structures), the user can also only use the first tightening device 12 to pressurize the limb, and the second emergency device 13 can be used depending on requirement.

Figure 11:
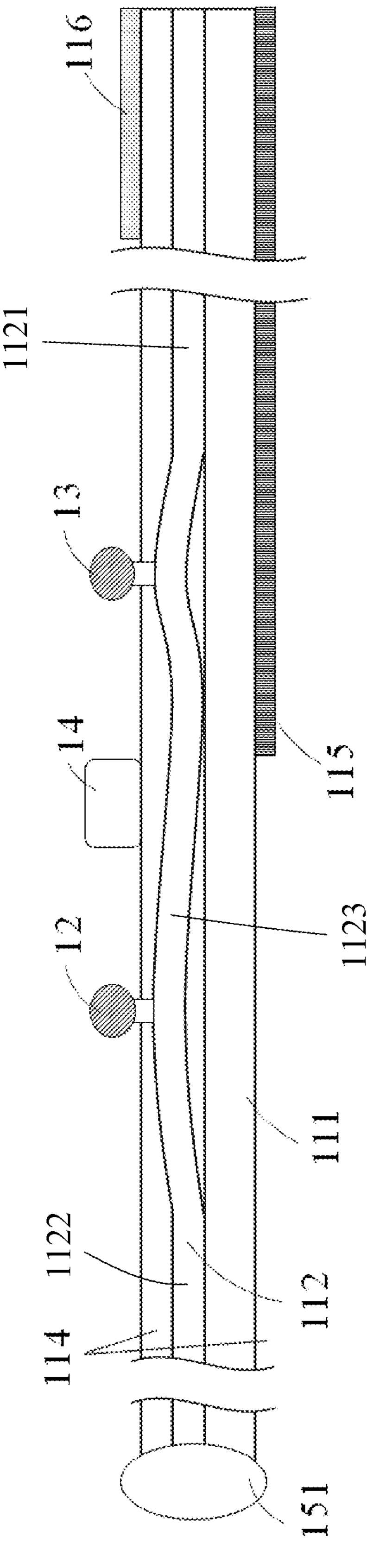
FIG. 11 is a third sectional view of the tourniquet with the multi-angle tightening device according to one embodiment of the present application.
Figure 12:
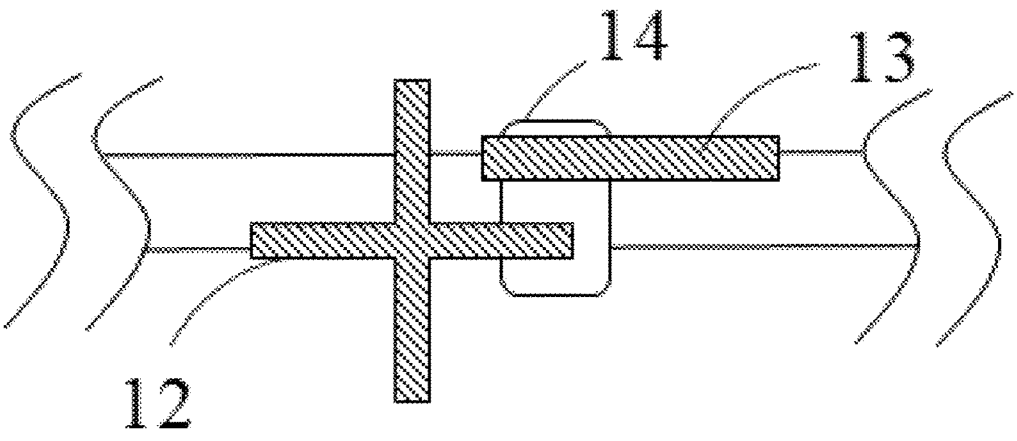
FIG. 12 is a fourth implementation schematic diagram of the tourniquet with the multi-angle tightening device according to one embodiment of the present application.

In one embodiment, the tourniquet main body 11 can include a first tightening strip 111, a second tightening strip 112, and a cover layer 114. As illustrated in FIG. 11, a first portion 1121 and a second portion 1122 of the second tightening strip 112 can be connected to the first tightening strip 111, and a third portion 1123 of the second tightening strip 112 is movably disposed on the first tightening strip 111. The cover layer 114 can cover the first tightening strip 111 and the second tightening strip 112. The first tightening device 12 and the second tightening device 13 are connected to the third portion 1123 of the second tightening strip 112 through an opening of the cover layer 114.

In detail, the first portion 1121 of the second tightening strip 112 can be sewed on the first tightening strip 111. One end of the first tightening strip 111 and the second portion 1122 of the second tightening strip 112 can be connected to the first buckle 151. Furthermore, as the third portion 1123 of the second tightening strip 112 is not sewed on the first tightening strip 111, so the third portion 1123 of the second tightening strip 112 is movably disposed on the first tightening strip 111.

Furthermore, the fixing element 14 includes at least one limit unit 143, a first curved portion 141, and a second curved portion 142. The at least one limit unit 143 can be disposed between the first curved portion 141 and the second curved portion 142. The first curved portion 141 forms a first groove. The second curved portion 142 forms a second groove. Concave directions of the first groove and the second groove are opposite.

Therefore, when the first tightening device 12 and the second tightening device 13 are rod members, if the first tightening device 12 and the second tightening device 13 are rotated, the second tightening strip 112 will move toward a top surface of the cover layer 114, causing the tourniquet main body 11 to be tightened and to pressurize a limb. Furthermore, in one embodiment, in order to make the first tightening device 12 and the second tightening device 13 be not easily damaged, the first tightening device 12 and the second tightening device 13 can include aluminum alloy.

Figure 13:
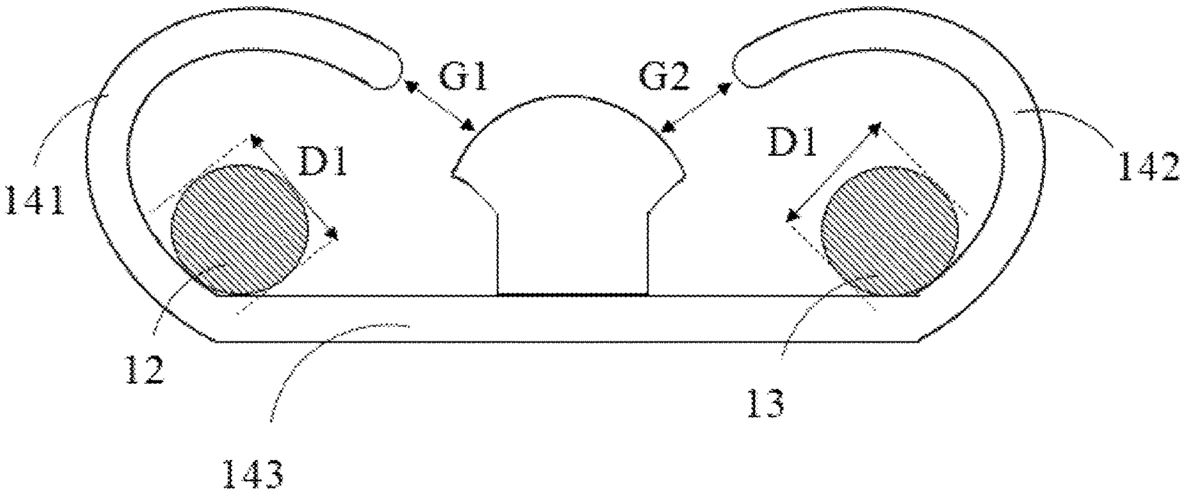
FIG. 13 is a fifth implementation schematic diagram of the tourniquet with the multi-angle tightening device according to one embodiment of the present application.
Figure 14:
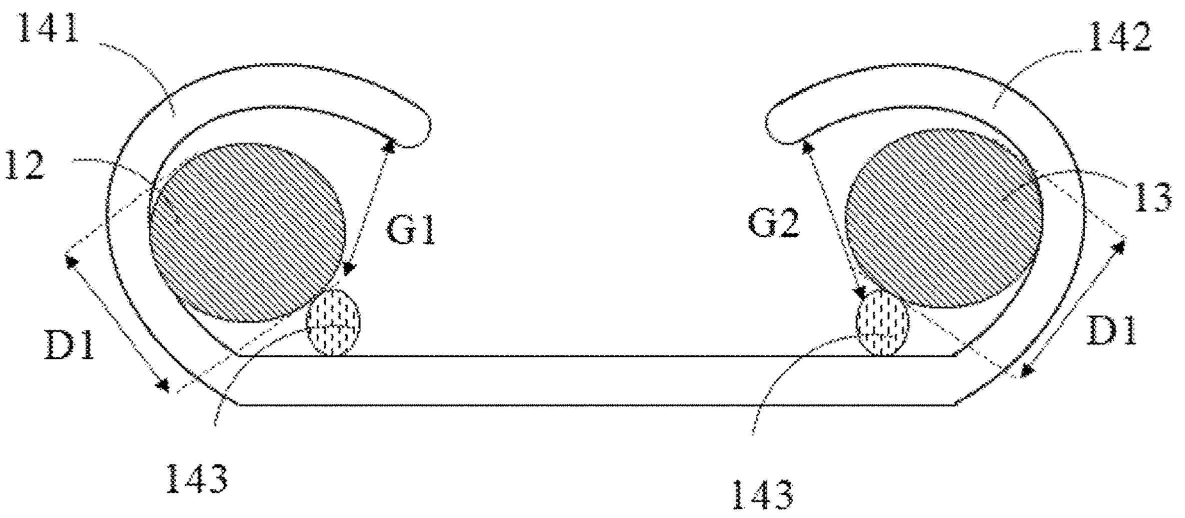
FIG. 14 is a sixth implementation schematic diagram of the tourniquet with the multi-angle tightening device according to one embodiment of the present application.

As illustrated in FIG. 13 or FIG. 14, in order to fix the first tightening device 12 and the second tightening device 13, the first tightening device 12 can be positioned against one of the first curved portion 141 or the second curved portion 142, and the second tightening device 13 can be positioned against another one of the first curved portion 141 or the second curved portion 142. In this configuration, even the pressure force of the first tightening device 12 to the first curved portion 141 or the second curved portion 142 is insufficient, the second tightening device 13 can further be used for secondary tightening to complete the process of pressing and hemostasis.

As illustrated in FIG. 13 and FIG. 14, in one embodiment, the limit unit 143 of the present application can be disposed between the first curved portion 141 and the second curved portion 142. For example, the limit unit 143 can be disposed at the center of the fixing element 14. The limiting unit 143 can be made of elastic material, such as polypropylene (Polypropylene, PP). A first interval G1 between the limit unit 143 and the top of the lateral wall of the first curved portion 141, and a second interval G2 between the limit unit 143 and the top of the lateral wall of the second curved portion 142 are less than a thickness D1 of the first tightening device 12 and the second tightening device 13.

Therefore, after the first tightening device 12 passes through the first curved portion 141 or the second curved portion 142, and the limit unit 143; the first tightening device 12 is restricted in the first curved portion 141 or the second curved portion 142. Similarly, after the second tightening device 13 passes through the first curved portion 141 or the second curved portion 142, and the limit unit 143; the second tightening device 13 is restricted in the first curved portion 141 or the second curved portion 142.

Furthermore, a top of the limit unit 143 can be a three-dimensional structure with a smooth curved surface such as a hemisphere, an ellipsoid, etc., and the tops of the lateral walls of the first curved portion 141 and the second curved portion 142 can be rounded or chamfered to facilitate the first tightening device 12 and the second tightening device 13 to slide through.

As illustrated in FIG. 14, in another embodiment, the limit unit 143 of the present application can also be disposed at another position. For example, two limit units 14 can be respectively disposed at the top of the lateral walls of the first curved portion 141 and the second curved portion 142 adjacent to the fixing element 14. The limiting units 143 can also be made of elastic material, such as polypropylene (Polypropylene, PP). The first interval G1 between the limit unit 143 and the top of the lateral wall of the first curved portion 141, and the second interval G2 between the limit unit 143 and the top of the lateral wall of the second curved portion 142 are less than the thickness D1 of the first tightening device 12 and the second tightening device 13.

Furthermore, in this embodiment, the first interval G1 between the limit unit 143 and the top of the lateral wall of the first curved portion 141, and the second interval G2 between the limit unit 143 and the top of the lateral wall of the second curved portion 142 are less than the thickness D1 of the first tightening device 12 and the second tightening device 13. Therefore, similar to the embodiment in which the limit unit 143 is disposed at the center of the fixing element 14, the first tightening device 12 and the second tightening device 13 can be restricted in the first curved portion 141 and the second curved portion 142.

Similarly, in this embodiment, the top of the limit unit 143 can also be a three-dimensional structure with a smooth curved surface such as a hemisphere, an ellipsoid, etc., and the tops of the lateral walls of the first curved portion 141 and the second curved portion 142 can be rounded or chamfered to facilitate the first tightening device 12 and the second tightening device 13 to slide through.

Figure 15:
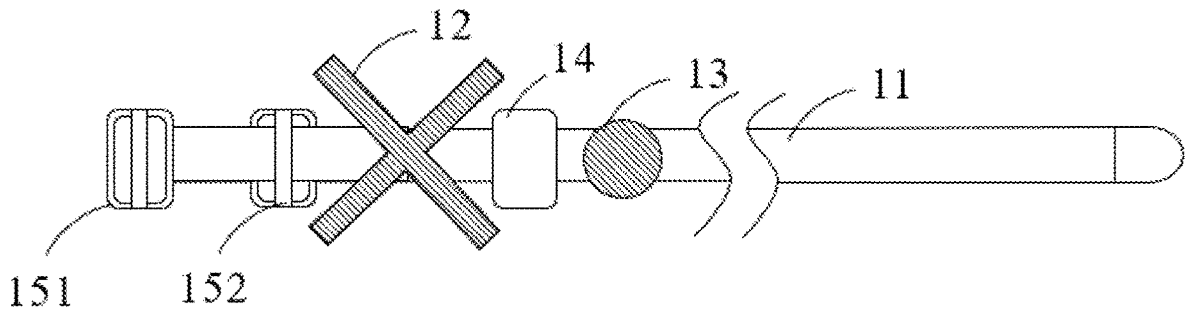
FIG. 15 is a fourth top view of the tourniquet with the multi-angle tightening device according to one embodiment of the present application.
Figure 16:
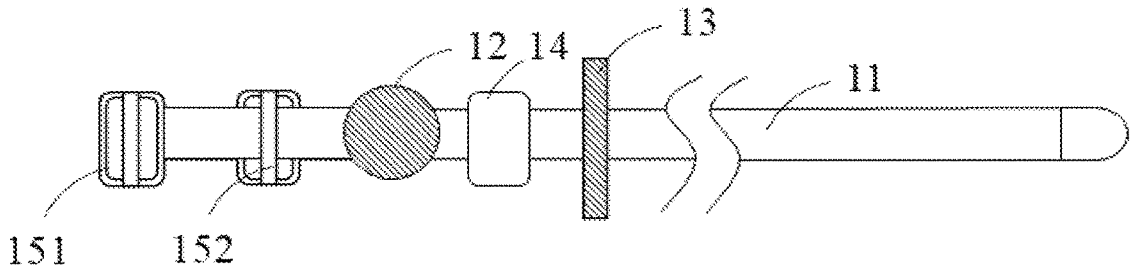
FIG. 16 is a fifth top view of the tourniquet with the multi-angle tightening device according to one embodiment of the present application.
Figure 17:
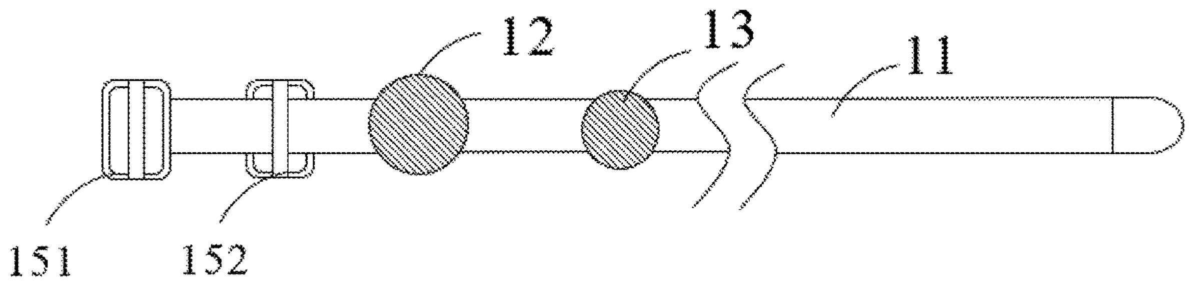
FIG. 17 is a sixth top view of the tourniquet with the multi-angle tightening device according to one embodiment of the present application.

Please refer to FIG. 15 to FIG. 17, the first tightening device 12 and the second tightening device 13 can not only be the rod member including the pillar-shaped structures, but also can be in other forms. As long as the plurality of tightening devices can make the tourniquet body 11 to pressurize the limbs multiple times, it should be regarded as the inventive concept of the present application.

In one embodiment, as illustrated in FIG. 15, the first tightening device 12 can be a rod member, and the second tightening device 13 can be a ratchet or other tightening device that can fix its own position. In one embodiment, as illustrated in FIG. 16, the first tightening device 12 can be a ratchet or other tightening device that can fix its own position, and the second tightening device 13 can be a rod member. In one embodiment, as illustrated in FIG. 17, the first tightening device 12 can be a ratchet or other tightening device that can fix its own position, and the second tightening device 13 can also be a ratchet or other tightening device that can fix its own position.

Different forms of the tourniquet with the multi-angle tightening device provided in FIG. 15 to FIG. 16 of the present application can also have the structures in FIG. 11 to FIG. 14. For example, the tourniquet main body 11 can also include the first tightening strip 111, the second tightening strip 112, and the cover layer 114. The first curved portion 141 and the second curved portion 142 can also be formed in the fixing element 14. Furthermore, there is only one rod member in FIG. 15 and FIG. 16, so after the tourniquet main body 11 is tightened to pressurize a limb, only one rod member is restricted by the first curved portion 141 or the second curved portion 142. Related descriptions can refer to the aforesaid structures, and will not be repeated herein again.

In FIG. 17, the tourniquet with the multi-angle tightening device includes a tourniquet main body 11, a first tightening device 12, and a second tightening device 13. The first tightening device 12 can be disposed on the tourniquet main body 11. The second tightening device 13 corresponds to the first tightening device 12 and is disposed on the tourniquet main body 11.

Furthermore, the first tightening device 12 can be a ratchet or other tightening device that can fix its own position, and the second tightening device 13 can also be a ratchet or other tightening device that can fix its own position. If the first tightening device 12 and the second tightening device 13 are both ratchets or other tightening devices that can fix their own positions, there is no need to additionally dispose the fixing element 14, and the aforesaid fixing effect and the effect of pressurizing the limb with the tourniquet main body 11 multiple times can thereby being achieved.

In addition, the tourniquet with the multi-angle tightening device provided in FIG. 17 can also have the structures in FIG. 9. Specifically, the tourniquet main body 11 can also include the first tightening strip 111, the second tightening strip 112, and the cover layer 114. Furthermore, there is no rod member in the structures disclosed in FIG. 17, so no fixing element 14 is required to be further disposed.

Figure 18:
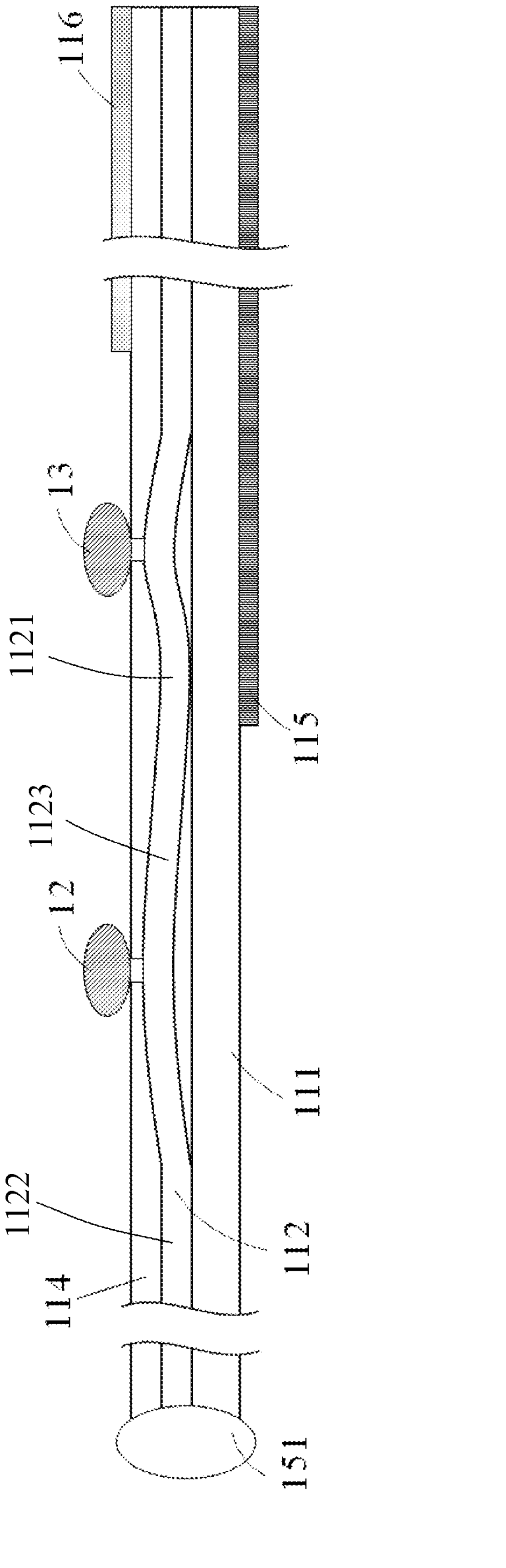
FIG. 18 is a fourth sectional view of the tourniquet with the multi-angle tightening device according to one embodiment of the present application.

In one embodiment, as illustrated in FIG. 17 and FIG. 9, the tourniquet main body 11 can include a first tightening strip 111, a second tightening strip 112, and a cover layer 114. As illustrated in FIG. 18, a first portion 1121 and a second portion 1122 of the second tightening strip 112 can be connected to the first tightening strip 111, and a third portion 1123 of the second tightening strip 112 is movably disposed on the first tightening strip 111. The cover layer 114 can cover the first tightening strip 111 and the second tightening strip 112. The first tightening device 12 and the second tightening device 13 are connected to the third portion 1123 of the second tightening strip 112 through an opening of the cover layer 114.

In detail, the first portion 1121 and the second portion 1122 of the second tightening strip 112 can be sewed on the first tightening strip 111. Furthermore, as the third portion 1123 of the second tightening strip 112 is not sewed on the first tightening strip 111, so the third portion 1123 of the second tightening strip 112 is movably disposed on the first tightening strip 111.

Therefore, when the first tightening device 12 and the second tightening device 13 are rod members, if the first tightening device 12 and the second tightening device 13 are rotated, the second tightening strip 112 will move toward a top surface of the cover layer 114, causing the tourniquet main body 11 to be tightened and to pressurize a limb.

In addition to the aforesaid disclosed structures, in one embodiment, as illustrated in FIG. 19 to FIG. 24, the tourniquet main body 11 can include a third tightening strip 113. A length of the third pressure strip 113 is shorter than that of the second tightening strip 112. Two ends of the third tightening strip 113 are connected to the first tightening strip 111, the second tightening strip 112, or the cover layer 114. The first tightening device 12 is connected to the third portion of the second tightening strip 112 through the opening of the cover layer 114, and the second tightening device 13 is connected to the third tightening strip 113.

In one embodiment, as illustrated in FIG. 9, FIG. 10, FIG. 12, FIG. 15 to FIG. 16, and FIG. 19, at least one first tightening device 12 or second tightening device 13 is a rod member. The tourniquet main body 11 can include a first tightening strip 111, a second tightening strip112, a third tightening strip 113, and a cover layer 114.

Figure 19:
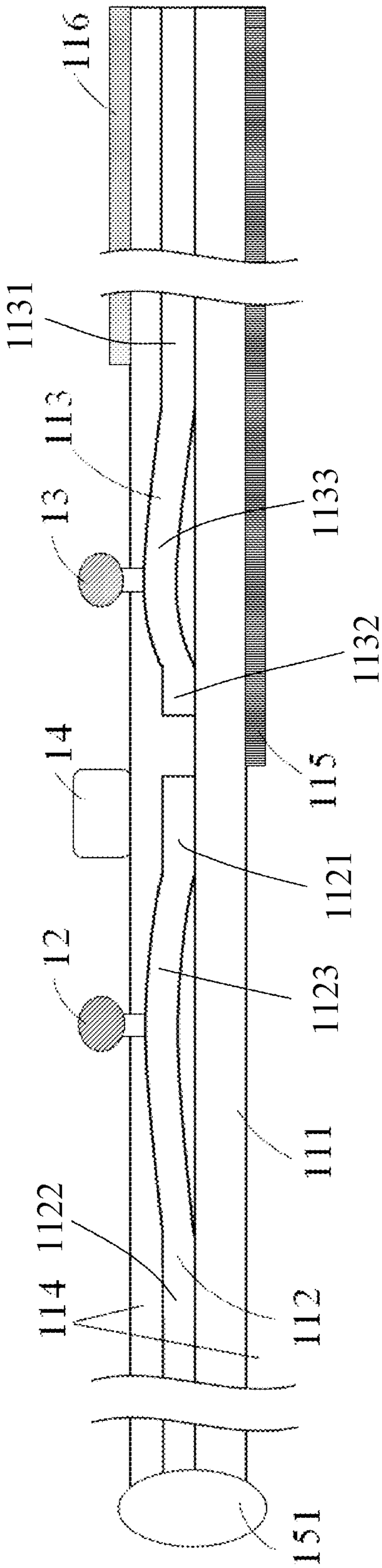
FIG. 19 is a fifth sectional view of the tourniquet with the multi-angle tightening device according to one embodiment of the present application.

As illustrated in FIG. 19, a first portion 1121 and a second portion 1122 of the second tightening strip 112 can be connected to the first tightening strip 111, and a third portion 1123 of the second tightening strip 112 is movably disposed on the first tightening strip 111. A first portion 1131 and a second portion 1132 of the third tightening strip 113 can be connected to the first tightening strip 111, and a third portion 1133 of the third tightening strip 113 is movably disposed on the first tightening strip 111. Both the second tightening strip 112 and the third tightening strip 113 can be sewed on the first tightening strip 111. The cover layer 114 can cover the first tightening strip 111, the second tightening strip 112, and the third tightening strip 113. The first tightening device 12 and the second tightening device 13 are connected to the second tightening strip 112 and the third portion 1133 of the third tightening strip 113 through the opening of the cover layer 114.

Additionally, regarding the relationship of the first tightening device 12, the second tightening device 13, and the fixing element 14, reference may be made to the aforesaid embodiments. In this embodiment, if the first tightening device 12 and the second tightening device 13 are rotated, the second tightening strip 112 can move toward the top surface of the cover layer 114, and the third tightening strip 113 can move toward the top surface of the cover layer 114, causing the tourniquet main body 11 to be tightened and to pressurize a limb.

In one embodiment, as illustrated in FIG. 9, FIG. 10, FIG. 12, FIG. 15 to FIG. 16, and FIG. 20, at least one first tightening device 12 or second tightening device 13 is a rod member. The tourniquet main body 11 can include a first tightening strip 111, a second tightening strip112, a third tightening strip 113, and a cover layer 114.

Figure 20:
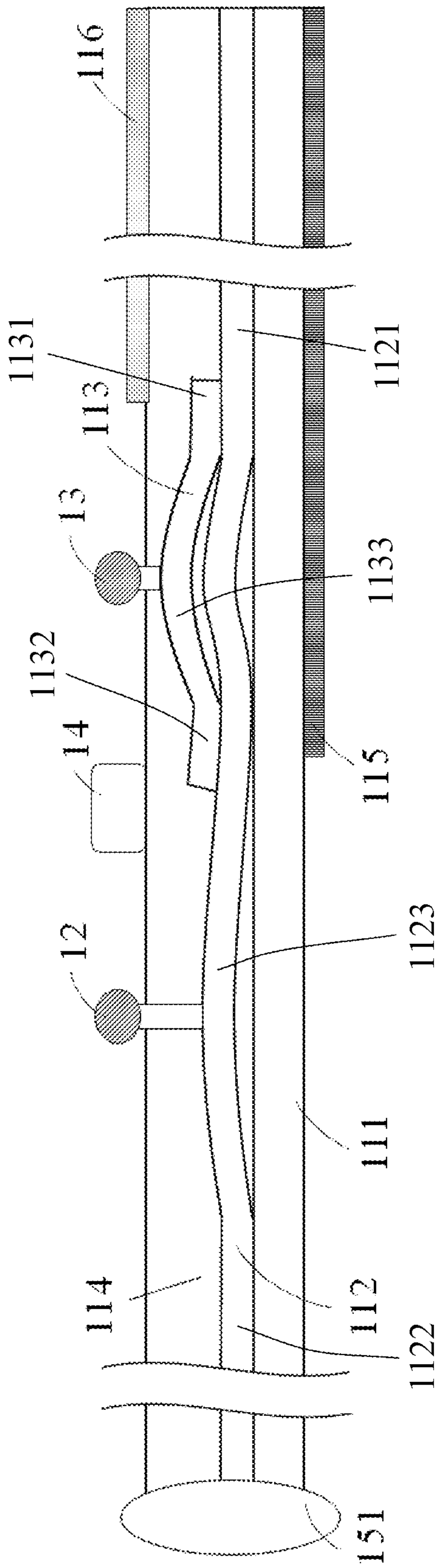
FIG. 20 is a sixth sectional view of the tourniquet with the multi-angle tightening device according to one embodiment of the present application.

As illustrated in FIG. 20, a first portion 1121 and a second portion 1122 of the second tightening strip 112 can be connected to the first tightening strip 111, and a third portion 1123 of the second tightening strip 112 is movably disposed on the first tightening strip 111. A first portion 1131 and a second portion 1132 of the third tightening strip 113 can be connected to the second tightening strip 112, and a third portion 1133 of the third tightening strip 113 is movably disposed on the second tightening strip 112. The second tightening strip 112 can be sewed on the first tightening strip 111. The third tightening strip 113 can be sewed on the first tightening strip 111. The cover layer 114 can cover the first tightening strip 111, the second tightening strip 112, and the third tightening strip 113. The first tightening device 12 and the second tightening device 13 are connected to the second tightening strip 112 and the third portion 1133 of the third tightening strip 113 through the opening of the cover layer 114.

Additionally, regarding the relationship of the first tightening device 12, the second tightening device 13, and the fixing element 14, reference may be made to the aforesaid embodiments. In this embodiment, if the first tightening device 12 and the second tightening device 13 are rotated, the second tightening strip 112 can move toward the top surface of the cover layer 114, and the third tightening strip 113 can move toward the top surface of the cover layer 114, causing the tourniquet main body 11 to be tightened and to pressurize a limb.

In one embodiment, as illustrated in FIG. 9, FIG. 10, FIG. 12, FIG. 15 to FIG. 16, and FIG. 21, at least one first tightening device 12 or second tightening device 13 is a rod member. Another one of the first tightening device 12 or second tightening device 13 is a ratchet or other tightening device that can fix its own position. The tourniquet main body 11 can include a first tightening strip 111, a second tightening strip112, a third tightening strip 113, and a cover layer 114.

Figure 21:
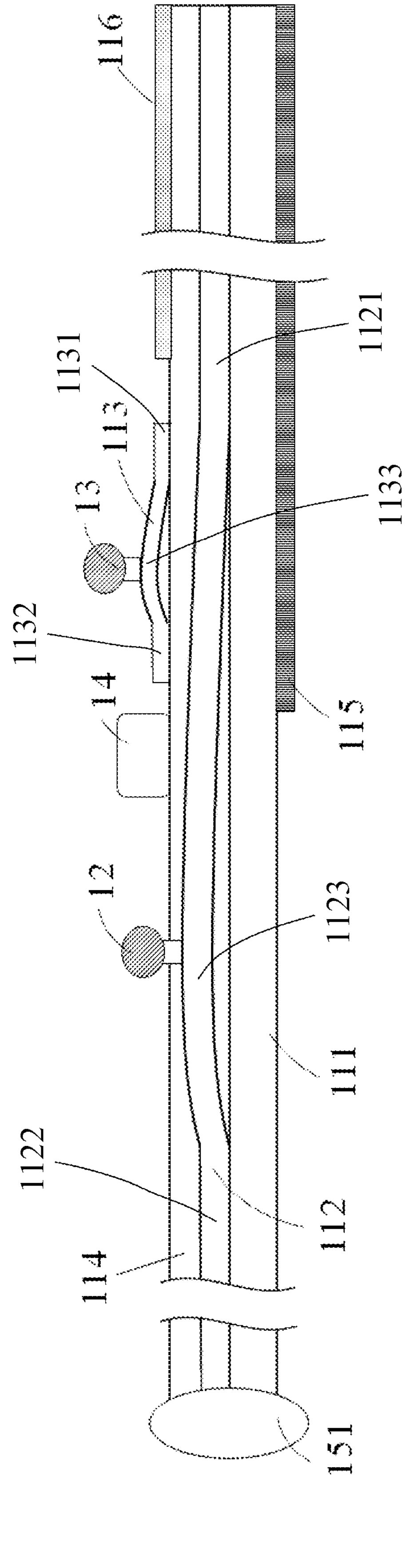
FIG. 21 is a seventh sectional view of the tourniquet with the multi-angle tightening device according to one embodiment of the present application.

As illustrated in FIG. 21, a first portion 1121 and a second portion 1122 of the second tightening strip 112 can be connected to the first tightening strip 111, and a third portion 1123 of the second tightening strip 112 is movably disposed on the first tightening strip 111. A first portion 1131 and a second portion 1132 of the third tightening strip 113 can be connected to the cover layer 114, and a third portion 1133 of the third tightening strip 113 is movably disposed on the cover layer 114. The second tightening strip 112 can be sewed on the first tightening strip 111. The third tightening strip 113 can be sewed on the cover layer 114. The cover layer 114 can cover the first tightening strip 111 and the second tightening strip 112. The first tightening device 12 is connected to the second tightening strip 112 and the third portion 1133 of the third tightening strip 113 through the opening of the cover layer 114.

Additionally, regarding the relationship of the first tightening device 12, the second tightening device 13, and the fixing element 14, reference may be made to the aforesaid embodiments. In this embodiment, if the first tightening device 12 and the second tightening device 13 are rotated, the second tightening strip 112 can move toward the top surface of the cover layer 114, and the third tightening strip 113 can roll up part of the cover layer 114, causing the tourniquet main body 11 to be tightened and to pressurize a limb.

In one embodiment, as illustrated in FIG. 17, and FIG. 22 to FIG. 24, the first tightening device 12 can be a ratchet or other tightening device that can fix its own position, and the second tightening device 13 can also be a ratchet or other tightening device that can fix its own position. The tourniquet main body 11 can include a first tightening strip 111, a second tightening strip112, a third tightening strip 113, and a cover layer 114.

Figure 22:
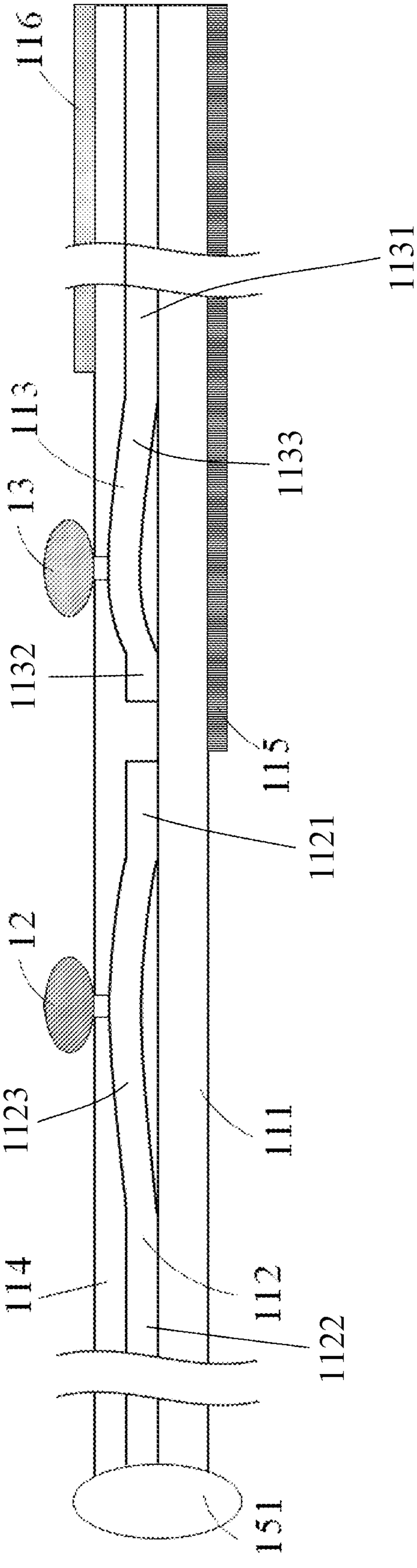
FIG. 22 is an eighth sectional view of the tourniquet with the multi-angle tightening device according to one embodiment of the present application.

As illustrated in FIG. 22, a first portion 1121 and a second portion 1122 of the second tightening strip 112 can be connected to the first tightening strip 111, and a third portion 1123 of the second tightening strip 112 is movably disposed on the first tightening strip 111. A first portion 1131 and a second portion 1132 of the third tightening strip 113 can be connected to the first tightening strip 111, and a third portion 1133 of the third tightening strip 113 is movably disposed on the first tightening strip 111. Both the second tightening strip 112 and the third tightening strip 113 can be sewed on the first tightening strip 111. The cover layer 114 can cover the first tightening strip 111, the second tightening strip 112, and the third tightening strip 113. The first tightening device 12 and the second tightening device 13 are connected to the second tightening strip 112 and the third portion 1133 of the third tightening strip 113 through the opening of the cover layer 114.

Additionally, in this embodiment, as the first tightening device 12 and the second tightening device 13 can be ratchets or other tightening devices that can fix their own positions, no fixing element 14 is additionally disposed, and related descriptions can refer to the aforesaid embodiments. In this embodiment, if the first tightening device 12 and the second tightening device 13 are rotated, the second tightening strip 112 can move toward the top surface of the cover layer 114, and the third tightening strip 113 can move toward the top surface of the cover layer 114, causing the tourniquet main body 11 to be tightened and to pressurize a limb.

In one embodiment, as illustrated in FIG. 17, and FIG. 22 to FIG. 24, the first tightening device 12 can be a ratchet or other tightening device that can fix its own position, and the second tightening device 13 can also be a ratchet or other tightening device that can fix its own position. The tourniquet main body 11 can include a first tightening strip 111, a second tightening strip112, a third tightening strip 113, and a cover layer 114.

Figure 23:
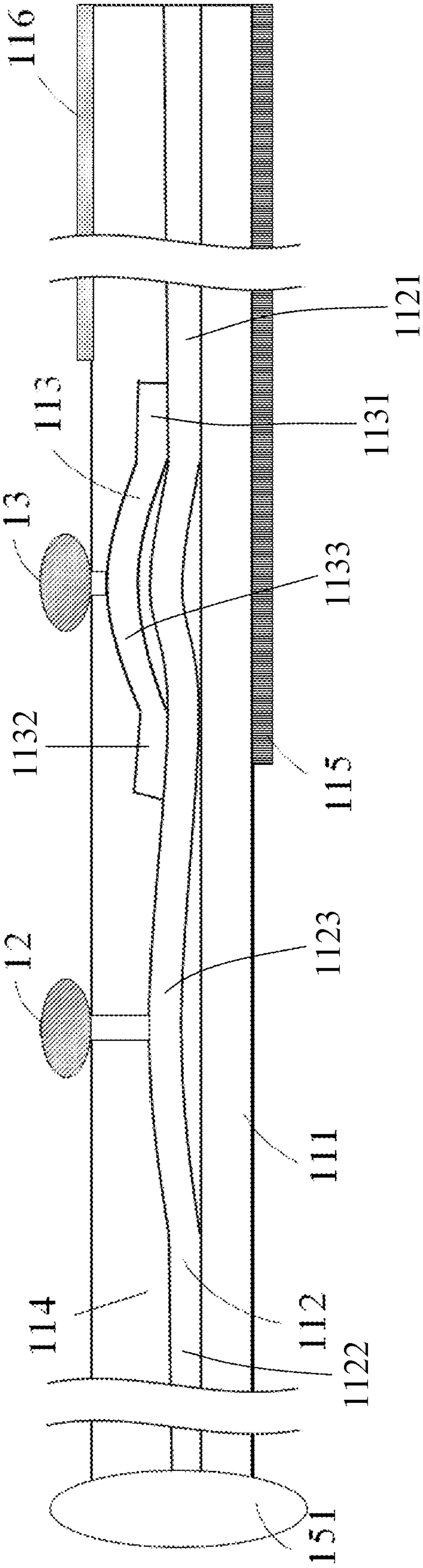
FIG. 23 is a ninth sectional view of the tourniquet with the multi-angle tightening device according to one embodiment of the present application.

As illustrated in FIG. 23, a first portion 1121 and a second portion 1122 of the second tightening strip 112 can be connected to the first tightening strip 111, and a third portion 1123 of the second tightening strip 112 is movably disposed on the first tightening strip 111. A first portion 1131 and a second portion 1132 of the third tightening strip 113 can be connected to the second tightening strip 112, and a third portion 1133 of the third tightening strip 113 is movably disposed on the second tightening strip 112. The second tightening strip 112 can be sewed on the first tightening strip 111. The third tightening strip 113 can be sewed on the first tightening strip 111. The cover layer 114 can cover the first tightening strip 111, the second tightening strip 112, and the third tightening strip 113. The first tightening device 12 and the second tightening device 13 are connected to the second tightening strip 112 and the third portion 1133 of the third tightening strip 113 through the opening of the cover layer 114.

Additionally, in this embodiment, as the first tightening device 12 and the second tightening device 13 can be ratchets or other tightening devices that can fix their own positions, no fixing element 14 is additionally added, and related descriptions can refer to the aforesaid embodiments. In this embodiment, if the first tightening device 12 and the second tightening device 13 are rotated, the second tightening strip 112 can move toward the top surface of the cover layer 114, and the third tightening strip 113 can move toward the top surface of the cover layer 114, causing the tourniquet main body 11 to be tightened and to pressurize a limb.

In one embodiment, as illustrated in FIG. 17, and FIG. 22 to FIG. 24, the first tightening device 12 can be a ratchet or other tightening device that can fix its own position, and the second tightening device 13 can also be a ratchet or other tightening device that can fix its own position. The tourniquet main body 11 can include a first tightening strip 111, a second tightening strip112, a third tightening strip 113, and a cover layer 114.

Figure 24:
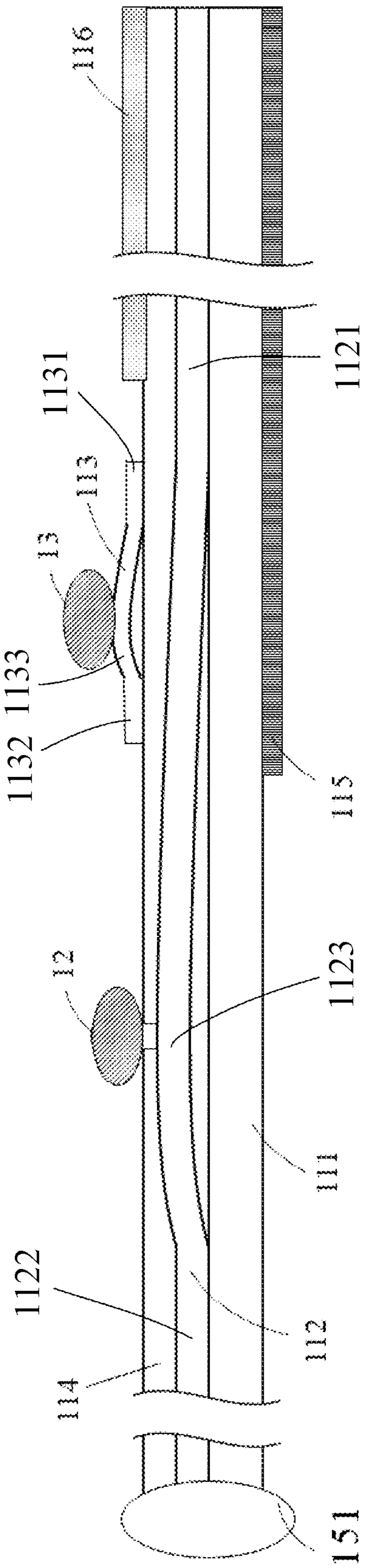
FIG. 24 is a tenth sectional view of the tourniquet with the multi-angle tightening device according to one embodiment of the present application.

As illustrated in FIG. 24, a first portion 1121 and a second portion 1122 of the second tightening strip 112 can be connected to the first tightening strip 111, and a third portion 1123 of the second tightening strip 112 is movably disposed on the first tightening strip 111. A first portion 1131 and a second portion 1132 of the third tightening strip 113 can be connected to the cover layer 114, and a third portion 1133 of the third tightening strip 113 is movably disposed on the cover layer 114. The second tightening strip 112 can be sewed on the first tightening strip 111. The third tightening strip 113 can be sewed on the cover layer 114. The cover layer 114 can cover the first tightening strip 111 and the second tightening strip 112. The first tightening device 12 is connected to the second tightening strip 112 and the third portion 1133 of the third tightening strip 113 through the opening of the cover layer 114.

Additionally, in this embodiment, no fixing element 14 is additionally disposed, and related descriptions can refer to the aforesaid embodiments. In this embodiment, if the first tightening device 12 and the second tightening device 13 are rotated, the second tightening strip 112 can move toward the top surface of the cover layer 114, and the third tightening strip 113 can roll up part of the cover layer 114, causing the tourniquet main body 11 to be tightened and to pressurize a limb.

Figure 25:
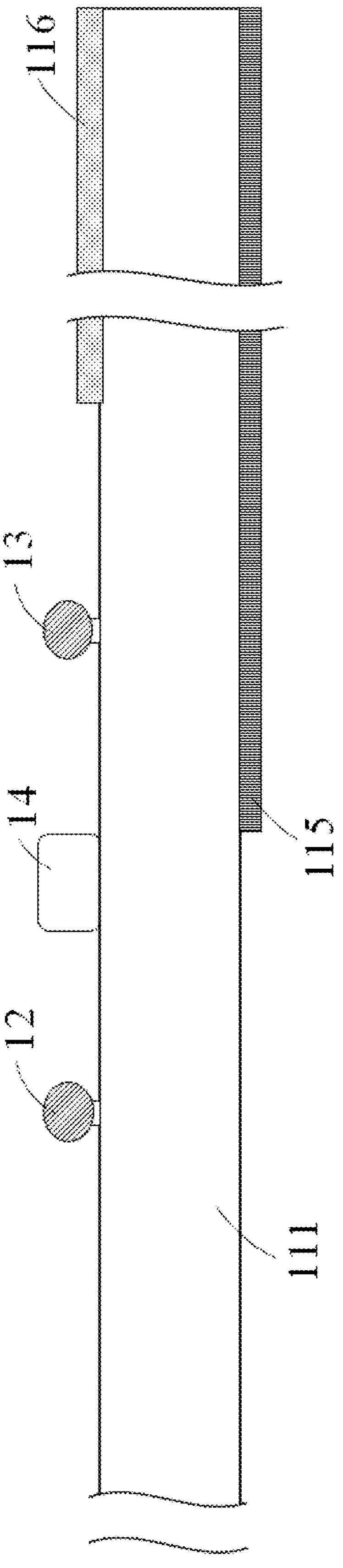
FIG. 25 is an eleventh sectional view of the tourniquet with the multi-angle tightening device according to one embodiment of the present application.
Figure 26:
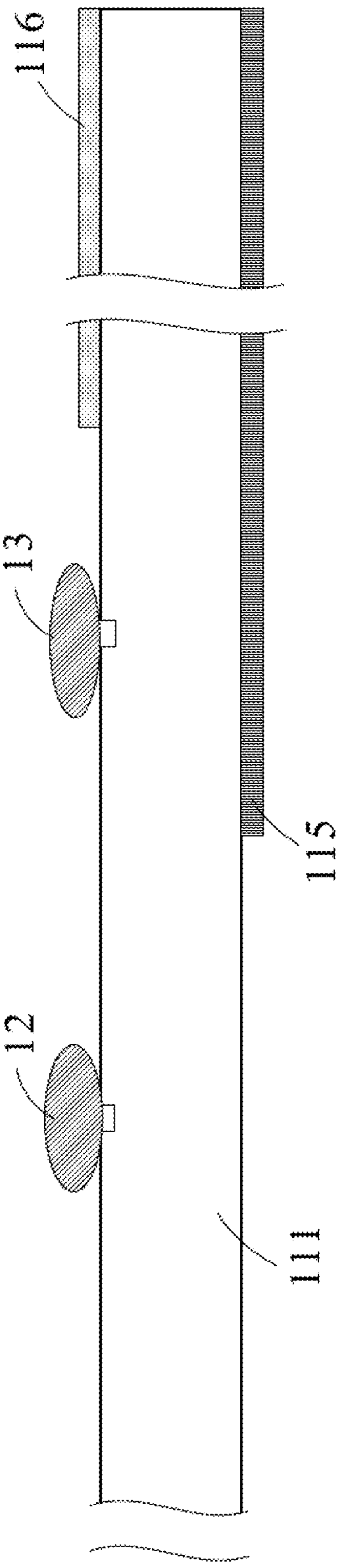
FIG. 26 is a twelfth sectional view of the tourniquet with the multi-angle tightening device according to one embodiment of the present application.
Figure 27:
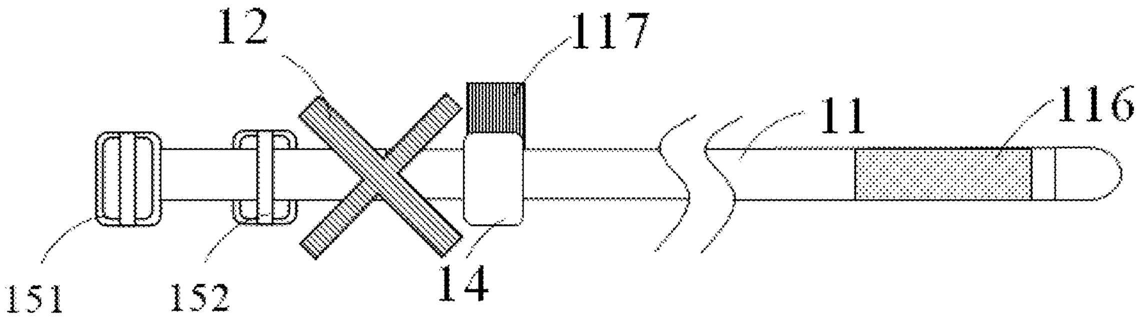
FIG. 27 is a seventh top view of the tourniquet with the multi-angle tightening device according to one embodiment of the present application.

In addition to the aforesaid embodiment including the second tightening strip 112 and the third tightening strip 113, the present application can also have other implementation forms. As illustrated in FIG. 25 and FIG. 26, the second tightening strip 112 and the third tightening strip 113 can also need not to be provided in the tourniquet with the multi-angle tightening device of the present application. In detail, the first tightening device 12 and the second tightening device 13 can be sewed on the first tightening strip 111. Furthermore, the first tightening device 12 and the second tightening device 13 can be rod members, ratchets or other tightening devices that can fix their own positions. When at least one of the first tightening device 12 and the second tightening device 13 is the rod member, as illustrated in FIG. 16, the fixing element 14 needs to be provided. When the first tightening device 12 is a ratchet or other tightening device that can fix its own position, and the second tightening device 13 can also be a ratchet or other tightening device that can fix its own position, and the fixing element 14 may not be disposed.

Furthermore, as illustrated in FIG. 4, FIG. 8, FIG. 11, and FIG. 18 to FIG. 26, the first attachment structure 115 and the second attachment structure 116 can be respectively disposed on a bottom surface and a top surface of the tourniquet main body 11. Therefore, after the tourniquet main body 11 is wound around, the first attachment structure 115 and the second attachment structure 116 are attached to each other.

In one embodiment, the first attachment structure 115 and the second attachment structure 116 can include Velcro or other re-attachable elements. Therefore, after a user easily wind the tourniquet main body 11 up, the user can attach the first attachment structure 115 and the second attachment structure 116 to each other at first, and then uses the first tightening device 12 and the second tightening device 13 to tighten the tourniquet main body 11 to pressurize the limb. In this embodiment, using the first attachment structure 115 and the second attachment structure 116 can make the tourniquet main body 11 be more convenient for usage, thereby reducing emergency time.

Additionally, in one embodiment, please refer to FIG. 17, in addition to the aforesaid structures, the tourniquet with multi-angle tightening device of the present application can also include a third attachment structure 117. The third attachment structure 117 can be connected to the tourniquet main body 11. The third attachment structure 117 is a strip structure, and one surface of the third attachment structure 117 is an attachment surface, which can be a Velcro or other re-attachable elements.

After the tourniquet main body 11 is wound around, the third attachment structure 117 can be attached to the first attachment structure 115 or the second attachment structure 116. Another surface of the third attachment structure 117 is a surface for writing. The time that the tourniquet body 11 has being wound around can be written by a user on the writing surface of the third adhesive structure 117, so as to avoid secondary injury caused by excessive pressurized time to a limb.

In one embodiment, one or both of the aforesaid first attachment structure 115 or the second attachment structure 116 can be omitted, and only the third attachment structure 117 is used to fix the tourniquet main body 11 after winding.

In summary, the tourniquet with the multi-angle tightening device of the present application has various implementation forms. In the tourniquet with the multi-angle tightening device of the present application, as the limb can be pressurized at multiple angles, the problem that different limb sizes cannot be reliably pressurized for hemostasis can be solved. The present application can increase the efficiency of using the tourniquet so that the tourniquet can be more convenient to use. Furthermore, as there is more than one tightening device, the tourniquet can still be used even any one of the tightening devices being failure, so the tourniquet with the multi-angle tightening device of the present application has better reliability.

The above are only examples, but are not for restriction. Any equivalent modifications or changes that do not depart from the spirit and scope of the present invention should be included in the scope of the claims.

What is claimed is:

1. A tourniquet with a multi-angle tightening device, comprising:
- a tourniquet main body;
- a first tightening device, rotatably disposed on the tourniquet main body, and comprising at least three pillar-shaped structures, wherein the at least three pillar-shaped structures respectively extends outward from a rotation center of the first tightening device, and there is a first width between the at least three pillar-shaped structures; and
- a fixing element, disposed adjacent to the first tightening device, and disposed on the tourniquet main body,
- wherein the first width is wider than a second width of the fixing element, a distance from the rotation center of the first tightening device to the fixing element is less than an extension length of any one of the at least three pillar-shaped structures from the rotation center;
- wherein the tourniquet main body comprises a first tightening strip, a second tightening strip, and a cover layer: a first portion and a second portion of the second tightening strip are connected to the first tightening strip, a third portion of the second tightening strip is movably disposed on the first tightening strip, and the cover layer covers the first tightening strip and the second tightening strip;
- wherein the first tightening device is connected to the third portion of the second tightening strip through an opening of the cover layer.

2. The tourniquet with the multi-angle tightening device as claimed in claim 1, wherein the fixing element comprises at least one limit unit, a first curved portion, and a second curved portion; the at least one limit unit is disposed between the first curved portion and the second curved portion, the first curved portion forms a first groove, and the second curved portion forms a second groove.

3. The tourniquet with the multi-angle tightening device as claimed in claim 2, wherein concave directions of the first groove and the second groove are opposite.

4. The tourniquet with the multi-angle tightening device as claimed in claim 3, wherein the first tightening device is positioned against one of the first curved portion or the second curved portion.

5. The tourniquet with the multi-angle tightening device as claimed in claim 4, wherein a first interval between the at least one limit unit and a top of a lateral wall of the first curved portion, and a second interval between the at least one limit unit and a top of a lateral wall of the second curved portion are less than a thickness of the first tightening device.

6. The tourniquet with the multi-angle tightening device as claimed in claim 1, comprising a second tightening device, wherein the second tightening device corresponds to the first tightening device and is disposed on the tourniquet main body, and the fixing element is disposed between the first tightening device and the second tightening device.

7. The tourniquet with the multi-angle tightening device as claimed in claim 1, wherein a first attachment structure and a second attachment structure are respectively disposed on a bottom surface and a top surface of the tourniquet main body; after the tourniquet main body is wound around, the first attachment structure and the second attachment structure are attached to each other.

8. A tourniquet with a multi-angle tightening device, comprising:

a tourniquet main body;

a first tightening device, rotatably disposed on the tourniquet main body; a second tightening device, corresponding to the first tightening device and disposed on the tourniquet main body; and a fixing element, disposed between the first tightening device and the second tightening device, and disposed on the tourniquet main body.

9. The tourniquet with the multi-angle tightening device as claimed in claim 7, wherein the first tightening device and the second tightening device are rod members.

10. The tourniquet with the multi-angle tightening device as claimed in claim 9, wherein the fixing element comprises at least one limit unit, a first curved portion, and a second curved portion; the at least one limit unit is disposed between the first curved portion and the second curved portion, the first curved portion forms a first groove, and the second curved portion forms a second groove.

11. The tourniquet with the multi-angle tightening device as claimed in claim 10, wherein concave directions of the first groove and the second groove are opposite.

12. A tourniquet with the multi-angle tightening device, comprising:

a tourniquet main body;

a first tightening device, rotatably disposed on the tourniquet main body; a second tightening device, corresponding to the first tightening device and disposed on the tourniquet main body; and a fixing element, disposed between the first tightening device and the second tightening device, disposed on the tourniquet main body, and comprising at least one limit unit, a first curved portion, and a second curved portion;

wherein the at least one limit unit is disposed between the first curved portion and the second curved portion, the first curved portion forms a first groove, and the second curved portion forms a second groove;

wherein the first tightening device and the second tightening device are rod members;

wherein concave directions of the first groove and the second groove are opposite;

wherein the first tightening device is positioned against one of the first curved portion or the second curved portion.

13. The tourniquet with the multi-angle tightening device as claimed in claim 12, wherein the second tightening device is positioned against another one of the first curved portion or the second curved portion.

* * * * *